(12) United States Patent
Stieglitz et al.

(10) Patent No.: US 6,908,470 B2
(45) Date of Patent: Jun. 21, 2005

(54) SIEVE ELECTRODE WHICH CAN BE CONNECTED TO A NERVE STUMP

(75) Inventors: Thomas Stieglitz, Ottweiler (DE); Jörg-Uwe Meyer, Ratzeburg (DE); Martin Schüttler, London (GB); Thomas Brinker, Hannover (DE)

(73) Assignee: Fraunhofer-Gesellschaft zur Foderung der angewandten Forschung e.V., Munich (DE)

(*) Notice: Subject to any disclaimer, the term of this patent is extended or adjusted under 35 U.S.C. 154(b) by 24 days.

(21) Appl. No.: 10/466,083

(22) PCT Filed: Jan. 10, 2002

(86) PCT No.: PCT/DE02/00048
§ 371 (c)(1),
(2), (4) Date: Dec. 1, 2003

(87) PCT Pub. No.: WO02/055151
PCT Pub. Date: Jul. 18, 2002

(65) Prior Publication Data
US 2004/0111140 A1 Jun. 10, 2004

(30) Foreign Application Priority Data
Jan. 11, 2001 (DE) .......................................... 101 01 026
Jan. 18, 2001 (DE) .......................................... 101 02 183

(51) Int. Cl.⁷ .............................................. A61N 1/04
(52) U.S. Cl. ..................................................... 606/118
(58) Field of Search ........................ 607/118; 606/152; 623/23.64, 66.1; 600/377

(56) References Cited

U.S. PATENT DOCUMENTS

| 3,833,002 A | * | 9/1974 | Palma .......................... 606/152 |
| 3,955,560 A | * | 5/1976 | Stein et al. .................. 600/377 |
| 4,623,355 A | * | 11/1986 | Sawruk ....................... 623/66.1 |
| 4,878,913 A | * | 11/1989 | Aebischer et al. ......... 623/23.64 |
| 5,030,225 A | * | 7/1991 | Aebischer et al. .......... 606/152 |
| 5,400,784 A | | 3/1995 | Durand et al. |
| 5,897,583 A | | 4/1999 | Meyer et al. |

FOREIGN PATENT DOCUMENTS

| WO | WO 93 20887 | 10/1993 |
| WO | WO 96 08290 | 3/1996 |

OTHER PUBLICATIONS

Stieglitz et al., "A Flexible, Light–Weight Multichannel Sieve Electrode With Integrated Cables For Interfacing Regenerating Peripheral Nerves", Sensors and Actuators A, Elsevier Sequoia S.A., Lausanne, Ch, vol. 60, No. 1–3, pp. 240–243, (May 1, 1997).

Abschlussbericht: Neuronen–Mikrosonde, Teilprojekt Nervenzellenkultur, IBMT Fraunhofer–Institut Biomedizinische Technik, pp. 29–31, (Sep. 2, 1999).

(Continued)

*Primary Examiner*—George Manuel
(74) *Attorney, Agent, or Firm*—Venable LLP; Robert Kinberg

(57) ABSTRACT

The present invention relates to a sieve electrode for connection to a nerve stump, which is composed of a thin flexible substrate (1) with a plurality of ports (2) for nerve filaments and several electrodes (3) that are disposed on at least some of said ports (2) on said substrate (1) and adapted for being electrically contacted via conductors (5) on said substrate (1), as well as of at least one counter-electrode (4). The substrate (1) presents tabs (6) protruding from the edge for fixing the substrate (1) on a face of the nerve stump, which serve, at the same time, as carrier of the counter electrode (4).

With this sieve electrode a neuro-technological interface is provided that permits a low-lesion contact with the nerve stump at a maximum of useable surface for the ports.

15 Claims, 2 Drawing Sheets

OTHER PUBLICATIONS

Wallmann et al., "Perforated Silicon Nerve Chips With Doped Registration Electrodes: In Vitro Performance And In Vivo Operation," IEEE Transactions on Biomedical Engineering, vol. 46, No. 9, pp. 1065–1073, (Sep. 1999).

Stieglitz et al., "Microtechnical Interfaces to Neurons," Manz A. Becker H. (eds), Microsystem Technology in Chemistry And Life Science, vol. 194, pp. 131–162, (1998).

* cited by examiner

SIEVE ELECTRODE WHICH CAN BE CONNECTED TO A NERVE STUMP

FIELD OF APPLICATION

The present invention relates to a sieve electrode for connection to a nerve stump, which is composed of a thin flexible substrate with a plurality of ports for nerve filaments and several electrodes that are disposed on at least some of said ports on said substrate and adapted for being electrically contacted via conductors on said substrate, as well as of at least one counter-electrode spaced from said ports, wherein said substrate presents tabs protruding from the edge for fixing said substrate on a face of the nerve stump.

Such sieve electrodes may be used particularly in the field of neuro-prosthetics. Neuro-prosthetics is a field dealing, on the one hand, with the control of organs by the electric stimulation of nerves by means of technological devices and, on the other hand, with the use of endogenous nerve signals for controlling technological prostheses and other assisting means. The implementation of these functions requires neuro-technological interfaces, i.e. interfaces between the body's own nerves and technological devices via which the nerves can be stimulated or nerve signals can be derived. For example, derived nerve signals can be used to control a technological prosthesis in the form of an artificial limp to perform a movement or to feed the instantaneous technological condition of the prosthesis via an appropriate stimulation of the nerves back to the patient, for instance by means of an instantaneous value representing an exerted pressure, an exerted force, an actuating distance and/or an actuating angle. The sieve electrode according to the present invention constitutes a neuro-technological interface for such an application.

PRIOR ART

The possibility of controlling artificial limbs by signals from nerves that were left over after a lesion due to amputation has been studied for a major period of time. The objective of these studies include the provision of a suitable implant that contacts the nerve stump and detects the nerve signals for transmission to the artificial limb by wireless communication so that the wearer of the implant will be able to control the prosthesis via his or her nerve signals. Such an application is schematically illustrated by way of example in FIG. 1. The Figure shows a nerve 10 in a patient's body, which has been severed due to the amputation of the forearm. A coupling interface 9 is fixed on the proximal nerve stump, for instance in the form of a sieve electrode according to the present invention, which is connected via a cable to another implant 12 for telemetric transmission of signals and energy. This implant 12 is equipped with an antenna and communicates with a corresponding further implant in the artificial limb 13 that replaces the forearm. In addition to an energy supply and driving units, a control system is provided in the limb 13, which controls the driving units on the basis of the received nerve signals for moving the limb. A principal problem in such an application is a stable functional and damage-free coupling of a technological structure such as that of the interface 9 to the nerve stump of the amputation site.

Configurations of such interfaces are known already from prior art, specifically in the form of cuffs or sieve electrodes. Approaches for implementation of the neuro-technological interface in the form of a sieve electrode have been studied since the beginning of the eighties of the last century. These sieve electrodes consist of a substrate including a plurality of through-holes or ports, so-called sieve holes, through which the regeneration of the nerve filaments (neuritis) takes place after the implantation of this sieve in the region of the nerve stump. The sieve electrodes, which are realised by micro-mechanical means, are manufactured from silicon or polyimide as substrate material, as a rule. Annular isolated electrodes around the sieve holes serve to derive nerve signals or to stimulate the nerve filaments electrically.

The problems of contacting the individual electrodes of the sieve electrode have meanwhile been solved by the monolithic integration of conductors and cable feeders into the structure produced by micro-mechanical means.

One example of a sieve electrode including a monolithic integrated feeder is mentioned in T. Stieglitz et al. "Sensors and Actuators" A 60 (1997, pages 240 to 243. That known sieve electrode comprises a thin substrate with a plurality of ports in the common manner, whereof some are enclosed by ring electrodes integrated on the substrate. The ring electrodes are contacted via conductors on the substrate, which extend via a feeder configured integrally in the substrate towards remote connector pads. During the implantation of the sieve electrode, the feeder is passed up to the body surface so that the connector pads and hence the individual electrodes can be contacted from there. The counter electrode, which is necessary for the function of this system, is configured with a large area on the outer periphery of the substrate in that known sieve electrode, covering a surface that corresponds to a multiple of the total area of the ring electrodes. The sieve electrode is fixed on the nerve stump via a rigid guiding passage fixedly connected to the substrate and extending in a direction orthogonal on the substrate surface, which passage is pushed over and fastened on the nerve stump during the implantation.

Such a configuration of the sieve electrode presents, however, the disadvantage that the guiding passage increases the weight of the entire microstructure and may furthermore contribute to a mechanical lesion of the nerves. On the other hand, the counter electrode requires a substantial area on the substrate, which is no longer available for ports for the regeneration of the nerve filaments. Proliferation of the nerve filaments through the substrate is not possible at the location of the counter electrode.

An improved sieve electrode is known from the Final report "Neuron Micro Probe" for the sub-project "Neurone Culture" of the Federal Ministry of Education and Research, dated Sep. 02, 1999, wherein the substrate presents tabs protruding on the edge, via which the substrate can be fixed on the nerve stump. These tabs may be sutured to the nerve stump through ports formed therein so that the application of comparatively rigid guiding passages will be avoided, which may result in lesion of the nerves.

Starting out from this prior art, the present invention is based on the problem of providing a sieve electrode for connection to a nerve stump as neuro-technological interface, which permits a low-lesion contacting of the nerve stump and presents a large useable area for the proliferation of the nerve filaments therethrough.

BRIEF DESCRIPTION OF THE INVENTION

The problem of the invention is solved by the sieve electrode according to Patent Claim 1 of record. Expedient embodiments of the sieve electrode are the subject matters of the dependent Claims.

The present sieve electrode for connection to a nerve stump is composed of a thin flexible substrate with a plurality of ports for nerve filaments and several electrodes that are disposed on at least some of said ports on said substrate and adapted for being electrically contacted via conductors on said substrate, as well as of at least one counter-electrode spaced from said ports. The substrate presents tabs protruding from the edge for fixing said substrate on a face of the nerve stump. The present sieve electrode is characterised by the provision that the at least one counter electrode is applied on at least one of the tabs rather than on the substrate.

Due to this design, a novel sieve electrode is provided for the electrical coupling to nerve ends that have lost their contact with the target organ as a result of lesions caused by the amputation of limbs and/or of other destructions of nerves. On account of the tabs provided on the substrate, which serve at the same time as carrier of the counter electrode(s) according to the invention, a simple means is achieved for fastening the sieve electrode on the nerve stump located above the lesion site. Due to their flexibility, the tabs permit a low-lesion contacting of the nerve stump. On account of the integration of the counter electrode(s) on the tabs, the entire substrate surface is available for the arrangement of the ports so that, at the same time, the ratio of the opening surface of the ports to the substrate surface is maximised as it is not necessary to reserve some space for large-area counter electrodes on the substrate. The arrangement of the counter electrodes on the tabs focuses the distribution of the electric field on the immediate vicinity of the electrode.

In a preferred embodiment, this interface provided by the sieve electrode comprises—in addition to the fastening structures designed as tabs and the entire electrode structures, i.e. the derivation or stimulating electrodes as well as the counter electrodes—also the electric conductors that are required for electrically contacting the electrodes and hence the nerve filaments, on the one hand, and for the electric connection to a telemetric energy and signal transmitter unit, on the other hand, which is schematically illustrated in FIG. 1 by way of example, or a controller or analyser unit outside the body.

Due to the preferably monolithic integration of the fixing tabs, electrodes, counter electrodes and the feeder with the electric conductors in a light-weight flexible micro structure a low-lesion neuro-surgical fixing on the nerve sheath (epineurium) of the nerve becomes possible.

A metallization surface as counter electrode is preferably arranged on several tabs, not only on one of the tabs, particularly with the arrangement of one respective counter electrode on each of the tabs. In a preferred embodiment, this plurality of counter electrodes distributed over the tabs are connected to constitute a single ring electrode that extends hence all around the nerve. With such a configuration, a potential gradient in a direction towards the nerve is created between the ring electrodes present on the sieve and this ring counter electrode. Due to the arrangement in symmetry relative to the nerve stump, good results are achieved in control of the nerve filaments or in the derivation of the nerve signals, respectively.

The tabs as carriers of the counter electrodes and for the simultaneous fixing of the sieve electrode on the nerve stump are preferably configured integrally in the substrate, which means that they are formed of the same substrate body. It goes without saying that these tabs must be adapted to be bent relative to the substrate surface for their proper envisaged fixing function. The sieve electrode is preferably made available with tabs already bent prior to its implantation, which tabs may extend in a direction approximately orthogonal on the substrate surface, for instance.

In a preferred embodiment, the substrate is integrally connected to a feeder on which the conductors coming from the electrodes and the counter electrode are continued up to an external connector. The feeder is preferably designed as thin narrow strip with conductors applied thereon, and in one embodiment of the present sieve electrode it is bent relative to the substrate surface.

The electrodes on the substrate are preferably configured as ring electrodes around the ports, as is known from prior art. These electrodes may, of course, also be disposed in another form, e.g. as punctiform electrodes between the holes. The number of the electrodes, which are possibly configured as ring electrodes, depends on the respective application and may vary up to a number corresponding to the number of the ports. The substrate, in its turn, as well as its dimensions and the dimensions of the feeder may be chosen in a comparable manner, as is known from the publication by Stieglitz et al. quoted by way of introduction. The same applies to the dimensions of the ports, the thickness and the material of the substrate and the feeder. The ports are preferably disposed on the substrate surface, however in correspondence with a hexagonal structure, as this arrangement results in a maximum number of ports on the substrate with a given diameter and spacing of these openings.

BRIEF DESCRIPTION OF THE DRAWINGS

In the following, the invention will be briefly described again by an embodiment, with reference to the Figures wherein.

WAYS OF RELEASING THE INVENTION

Figure 1:
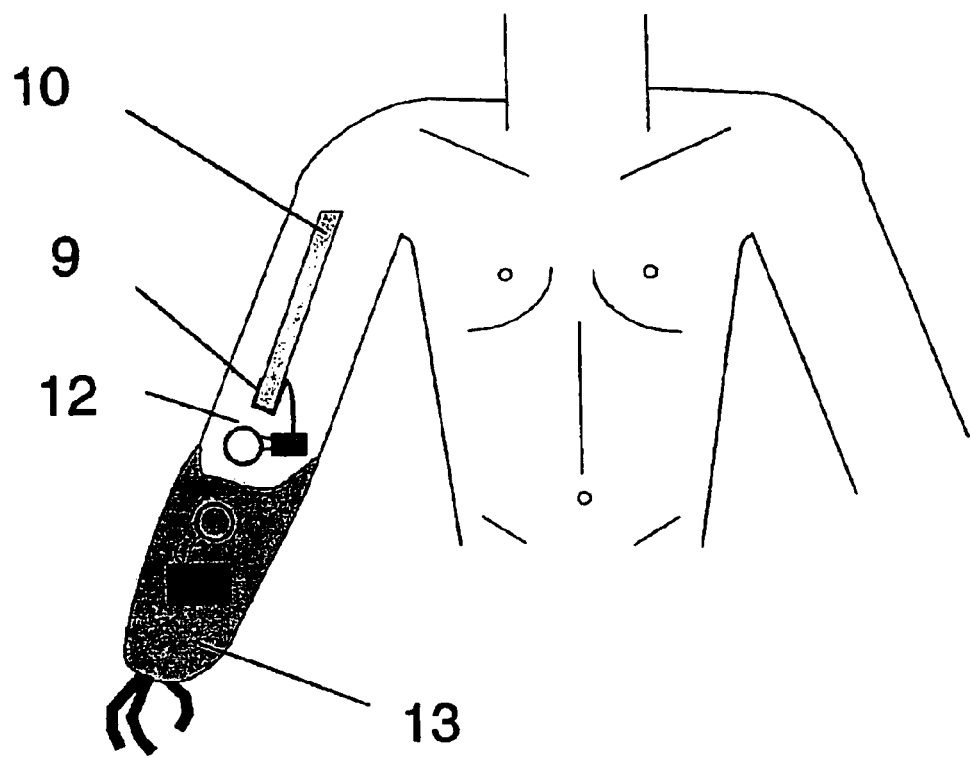
FIG. 1 is a schematic view of an example of an application of a neuro-technological interface according to the present invention for communication with an artificial limb.

The arrangement according to FIG. 1, which illustrates a potential application of the flexible sieve electrode according to the present invention, has already been explained in the context of the discussion of the approaches made in prior art.

Figure 2:
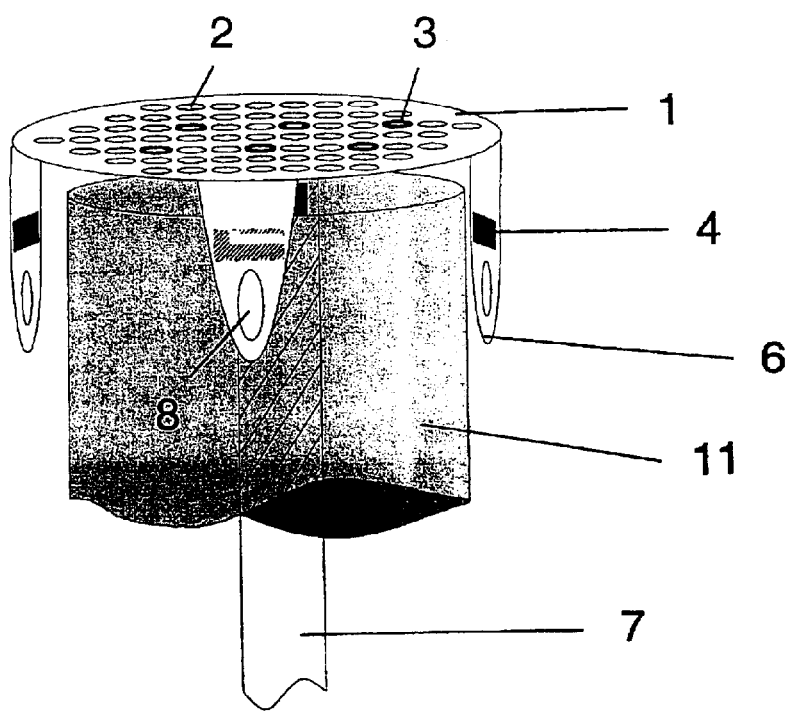
FIG. 2 illustrates an embodiment of the present sieve electrode in a schematic view.

FIG. 2 illustrates one embodiment of the inventive sieve electrode in a schematic view. In that Figure, the thin flexible substrate 1 of the sieve electrode can be seen that presents a plurality of ports 2 for the proliferation of nerve filaments therethrough. In the present embodiment, polyimide is used as substrate material as well as for insulation of the conductors (not illustrated) and electrodes that are integrated on this substrate 1. Ring electrodes 3 are provided on isolated ports 2 in the substrate 1, which can be electrically contacted via the non-illustrated conductors. Tabs 6 can be seen on the substrate 1, which are bent at an approximately right angle for fixing the sieve electrode in its entirety on a nerve stump 11. The tabs include holes 8 permitting the passage of surgical suturing material for fastening the tabs 6 on the nerve stump 11. Counter electrodes 4 are integrated into the tabs 6, which can equally be contacted via non-illustrated conductors in the tabs 6 and the substrate 1.

The Figure moreover illustrates a feeder or supply line 7 that is integrally connected to the substrate 1 and in which the conductors leading to the electrodes 3 or the counter electrodes 4, respectively, are continued up to a non-illustrated external connector. In this example, this feeder 7 is bent through roughly 90° relative to the substrate surface in the same manner as the tabs 6 and can equally be sutured to the nerve stump 11. This feeder may, of course, also be guided away from the substrate 1 in another direction. Connector surfaces or a plug contact are provided on the end of the feeder line for the external contact with the sieve electrode. Conductors 5 and electrodes 3, 4 consist of a thin-film metallization, with the conductors 5 and the non-illustrated connecting contacts possibly consisting of materials such as gold whilst the ring electrodes 3 and the counter electrodes 4 may consist of materials such as platinum or iridium (oxide).

The ring electrodes 3 may be uniformly distributed on the sieve surface or only in certain areas thereof, i.e. the surface of the substrate 1, in an arrangement around the ports 2.

The substrate 1, which is made of a polyimide sheet in this example, may present a diameter of roughly 2 mm and a thickness of approximately 10 µm, for example. The ports or through-holes, respectively, may present here a diameter of roughly 40 µm. The metal layers for the electrodes and conductors may be applied and structured, for instance, by a sputtering and a lift-off process. For exposition of the electrodes 3 by etching, for structuring of the holes 2 and for separation of the entire structures the technique of reactive ion etching (RIF) may be employed. Those skilled in the art is, of course, well aware of other techniques, too, from semiconductor technology for the provision of such a structure.

For bending the tabs 6, which are configured integrally with the substrate 1, the substrate may be inserted into a dedicated tool, for instance, that bends the tabs 6 when it is closed. This system in the closed condition is then placed into a furnace and tempered there at roughly 300° C. for approximately 1 hour. This process furnishes a permanent plastic deformation of the polyimide of which the substrate 1 and the tabs 6 are formed so that after cooling the tabs retain their desired bent shape.

Figure 3:
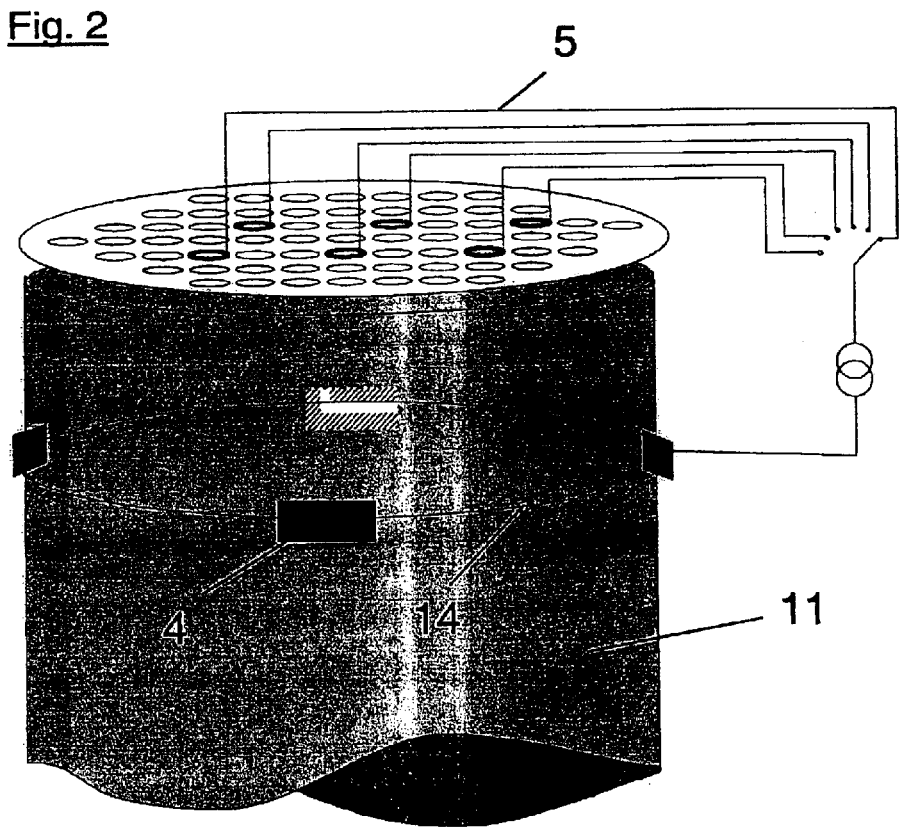
FIG. 3 shows an example of the connection of the electrodes in the sieve electrode according to FIG. 2.

FIG. 3 finally shows a strongly schematic view of the same arrangement as that illustrated in FIG. 2 with a potential connection of the six ring electrodes 3 and four counter electrodes 4, illustrated by way of example. As a matter of fact, however, the conductors 5, 14 for this connection extend on the substrate 1 or in the tabs 6, respectively. In this example, a connection 14 of the counter electrodes 4 with an individual ring electrode is illustrated. To this end, the counter electrodes 4 are interconnected on the sieve structure and passed out by a single contact via the feeder 7. They may be connected by an appropriate external control via the feeder 7 for electrical stimulation and/or the derivation of nerve signals to individual ring electrodes, or even simultaneously to several ring electrodes 3.

LIST OF REFERENCE NUMERALS 1 flexible substrate
2 ports, sieve holes
3 derivation or control electrodes, respectively
4 counter electrodes
5 conductors
6 flexible tabs
7 flexible feeder
8 holes on the tabs
9 coupling site on the nerve stump
10 nerve
11 nerve stump
12 implant with telemetric signal and energy transmitter
13 artificial limb
14 connecting line

What is claimed is:

1. Sieve electrode for connection to a nerve stump, which is composed of a thin flexible substrate (1) with a plurality of ports (2) for nerve filaments and several electrodes (3) that are disposed on at least some of said ports (2) on said substrate (1) and adapted for being electrically contacted via conductors (5) on said substrate (1), as well as of at least one counter-electrode (4) spaced from said ports (2), wherein said substrate (1) presents tabs (6) protruding from the edge for fixing said substrate (1) on a face of the nerve stump, characterised in that
at least one counter electrode (4) is applied on at least one of said tabs (6).

2. Sieve electrode according to claim 1, characterised in
that counter electrodes (4) are applied on several tabs (6).

3. Sieve electrode according to claim 2 characterised in
that said counter electrodes (4) on said tabs (6) are connected to form a ring electrode.

4. Sieve electrode according to claim 1, characterised in
that conductors (5) are formed on said tabs (6) and on said substrate (1) as electric feeders leading to said counter electrodes (4).

5. Sieve electrode according to claim 1, characterised in
that said tabs (6) are formed integrally with said substrate (1).

6. Sieve electrode according to claim 1, characterised in
that said tabs (6) are bent relative to the surface of said substrate.

7. Sieve electrode according to claim 1, characterised in
that said substrate (1) is connected to a feeder (7) by which an electric connection is established via said conductors (5) with said electrodes (3) and said counter electrode (4).

8. Sieve electrode according to claim 7, characterised in
that said feeder (7) consists of a thin strip with conductors, which is formed integrally with said substrate (1).

9. Sieve electrode according to claim 7, characterised in
that said feeder (7) is bent relative to the surface of said substrate.

10. Sieve electrode according to claim 9, characterised in
that said electrodes (3) are configured as ring electrodes around said ports (2).

11. Sieve electrode according to claims 1, characterised in
that said electrodes (3), counter electrodes (4) and conductors (5) are integrated into said substrate (1) or said tabs (6), respectively.

12. Sieve electrode according to claim 1, characterised in
that said tabs (6) present at least one through-hole (8) through which said tabs (6) maybe sutured to the nerve stump.

13. Sieve electrode according to claim 1, characterised in that said substrate (1) has a disk-shaped configuration.

14. Sieve electrode according to claim 1, characterised in that said substrate (1) has a thickness of roughly 10 μm or less.

15. Sieve electrode according to claim 1, characterised in that said ports (2) are disposed in a hexagonal structure in said substrate (1).

* * * * *